United States Patent [19]

Bauer et al.

[11] 4,119,671

[45] Oct. 10, 1978

[54] PROCESS FOR THE PREPARATION OF HYDROXYBENZALDEHYDES

[75] Inventors: Kurt Bauer, Holzminden; Reiner Mölleken, Golmbach Ortsteil Warbsen; Helmut Fiege, Leverkusen; Karlfried Wedemeyer, Cologne, all of Germany

[73] Assignee: Bayer Aktiengesellschaft, Leverkusen, Germany

[21] Appl. No.: 792,425

[22] Filed: Apr. 29, 1977

[30] Foreign Application Priority Data

May 7, 1976 [DE] Fed. Rep. of Germany ....... 2620254

[51] Int. Cl.² ............................................. C07C 45/16
[52] U.S. Cl. ................................. 260/600 R; 562/477

[58] Field of Search ........................ 260/600 R, 521 B

[56] References Cited

U.S. PATENT DOCUMENTS

| 3,321,526 | 5/1967 | Marchand et al. | 260/600 R |
| 3,673,257 | 6/1972 | DiBella | 260/600 R |
| 4,026,950 | 5/1977 | Le Ludec | 260/600 R |

*Primary Examiner*—Bernard Helfin
*Attorney, Agent, or Firm*—Burgess, Dinklage & Sprung

[57] ABSTRACT

Salicylaldehyde and other hydroxybenzaldehydes are prepared by oxydation of a hydroxybenzyl alcohol in the presence of a platinum metal catalyst and lead, silver, tellurium or tin or compounds thereof as activator.

8 Claims, No Drawings

PROCESS FOR THE PREPARATION OF HYDROXYBENZALDEHYDES

The invention relates to a process for the preparation of hydroxybenzaldehydes by oxidation of hydroxybenzyl alcohols with oxygen or oxygen-containing gases in aqueous-alkaline media which optionally contain organic solvents, at temperatures of up to 100° C. in the presence of platinum metal catalysts.

It is known from DT-AS (German Published Specification No.) 1,188,069 to oxidise hydroxybenzyl alcohols, especially o-hydroxybenzyl alcohol, in aqueous-alkaline media with oxygen or oxygen-containing gases in the presence of platinum metal catalysts, for example platinum catalysts and palladium catalysts, to give hydroxybenzaldehydes. In order to avoid the disadvantages to which these processes are subject, for example the necessity for the use of large amounts of catalyst, it is proposed in DT-AS (German Published Specification No.) 1,188,069 to add boric acid as an activator when palladium catalysts are used. Despite ths activator, however, large amounts of palladium, long reaction times and considerable amounts of alkali metal hydroxide are still required in order to achieve satisfactory yields. Moreover, the boric acid also has to be employed in considerable amounts (see Example 1 where, per mol of saligenin to be oxidised, 2 mols of potassium hydroxide, 1,240 mg of palladium and 62 g of crystalline boric acid, and a reaction time of 11 hours, are employed in order to achieve an 83.5% yield of salicylaldehyde).

In U.S. Pat. No. 3,673,257, cadmium, cadmium-tetramine, cerium, indium, lanthanum, copper, yttrium, magnesium, uranyl or zinc ions are proposed as oxidation accelerators. However, no decisive reduction in the amount of platinum metal catalysts is achieved even by the addition of these activators and the amounts of activator required are uneconomically high. In order to oxidise one mol of saligenin, for example, 1,250 mg of platinum and 2 mols of cadmium hydroxide are employed (see Example 1). The yield of salicylaldehyde in this case is 96% of theory. However, if the amount of platinum catayst is reduced to 530 mg per mol of saligenin, even the use of the preferred activator, that is to say cadmium-tetramine hydroxide, and 2 mols of sodium hydroxide gives a salicylaldehyde yield of only 82% of theory. On the other hand, 2.1% of salicylic acid and 16.7% of tar form as the by-product. As the amount of platinum is reduced and the alkali metal hydroxide/saligenin ratio decreases, the yield falls and the reaction time and amount of tar increase considerably (see Table V).

The known processes require catalysts with relatively high metal contents, long reaction times and considerable amounts of expensive platinum metals, the re-use of which is severely restricted because of the amounts of tar formed during the reactions. Moreover, the high amount of alkali metal hydroxide to be used per mol of hydroxybenzyl alcohol is a disadvantage since, in order to isolate the aldehyde, the alkali has to be neutralised and, consequently, a high alkali/hydroxybenzyl alcohol ratio, apart from the alkali consumption as such, leads to a corresponding increased load on the effluent due to salts.

The object on which the invention is based is, therefore, to avoid the disadvantages to which the known processes for the oxidation of hydroxybenzyl alcohols with oxygen or oxygen-containing gases in the presence of platinum metal catalysts are subject.

This object is achieved according to the invention by carrying out the oxidation in the presence of lead, silver, tellurium and/or tin and/or compounds thereof.

The advantages achieved by means of the invention are that, due to the presence of the metals to be used according to the invention, the consumption of the platinum metal is considerably reduced, the formation of resin during the oxidation is virtually completely prevented and the amount of alkali required can be considerably reduced. The reaction time is also considerably shorter than in the case of the known processes and the yields of aldehyde are in most cases also better than those of the known processes.

Amongst the metals to be used according to the invention, silver and, above all, lead have proved particularly suitable.

The amounts in which the activators to be used according to the invention are employed can vary within wide limits. The activator effect is already clearly noticeable with additions of $5 \times 10^{-6}$ mols of metal or metal compound per mol of hydroxymethyl group. It is also possible to employ 0.1 mol or more of activator per mol of hydroxymethyl group but these high additions in general bring no advantage. In general, additions of $1 \times 10^{-5}$ to $1 \times 10^{-2}$ mols, and preferably of $2 \times 10^{-5}$ to $1 \times 10^{-2}$ mols, of metal per mol of hydroxymethyl group to be oxidised have proved suitable. When silver is used as the activator, the range preferably employed is from $1 \times 10^{-3}$ to $1 \times 10^{-1}$ mol of silver per mol of hydroxymethyl group.

The metals to be used according to the invention can be employed as such, that is to say in the form of the element, and/or in the form of their compounds, for example as oxides or salts, for example nitrates, sulphates, borates, acetates, phenolates and the like.

Combinations of these activators with one another and/or with other elements or compounds which are not claimed as activators can also be used. The activators according to the invention can be present in different valency stages and also mixed valency stages; it is also possible for changes in the valency to take place during the reaction. If the activators are not already added in the form of oxides and/or hydroxides, it is possible for them to be wholly or partially converted into these compounds in an alkaline medium. After the reaction, the platinum metal catalyst can be filtered off together with the sparingly soluble activator and re-used in further oxidations. Any losses of platinum metal catalyst and/or activator are optionally to be made up.

The activator can be added to the reaction components in the form of a solid, preferably in a finely divided form, or in the form of a solution. The activator can also already be added during the preparation of the platinum metal catalyst, or the platinum metal catalyst can be impregnated with the activator. The activator can also serve as the support material for the platinum metal.

"Platinum metals", which are employed as catalysts in the process according to the invention, are to be understood as the metals platinum, palladium, rhodium, iridium, ruthenium and osmium, which chemically are closely related and usually occur together in nature. The platinum metals platinum and palladium are preferably employed.

The platinum metals used as catalysts can be added to the reaction components in very diverse forms, for example in the form of the element, that is to say of the metal, for example as so-called black, in combination with other platinum metals or in the form of compounds, for example as oxides, or also in the form of other compounds.

The platinum metals can also be applied to supports. Suitable supports are, for example, active charcoals, graphite, kieselguhr, silica gel, spinels, aluminium oxide, asbestos, calcium carbonate, magnesium carbonate or barium sulphate, or also organic support materials. Active charcoals, for example cheap pulverulent active charcoals produced from wood, which are frequently used for decolorising purposes, have provded particularly useful.

The platinum metal content of these supported catalysts can vary within wide limits. Supported catalysts which have a platinum metal content of less than 6% by weight, and especially those which have contents of 0.1 to 2.5% by weight of platinum metal, have proved particularly suitable.

The amounts in which the platinum metal catalysts are used can vary within wide limits. The amounts depend on the desired rate of oxidation, of the nature of the hydroxybenzyl alcohol to be oxidised, on the form of catalyst, on the type and amount of activator and the like and in a particular case can easily be determined by preliminary experiments. Thus, when the oxidation of saligenin is carried out in the presence of lead compounds as the activator, a salicylaldehyde yield of 90 to 97% of theory is already achieved within 20 minutes, without a significant production of tar, when only 62 mg of platinum are present per mol of saligenin. If longer oxidation times are accepted, it is also possible to carry out the reaction in the presence of even smaller amounts of platinum, for example 10 mg of platinum per mol of saligenin. In this case the oxidation takes 10 hours and the yield is 84 or 91% of theory.

In general, the amount of platinum required per mol of hydroxybenzyl alcohol is less than 500 mg and in most cases adequately high rates of reaction are achieved with 10 to 150 mg of platinum metal per mol of hydroxymethyl group to be oxidised.

Since the formation of tar is virtually completely prevented by the use of the activators according to the invention, the catalyst can be used repeatedly, for example more than 30 times. Because of this re-use, the consumption of platinum metal catalyst per mol of hydroxybenzyl alcohol can be reduced to 2 mg and less without the aldehyde yield falling and further addition of activator being necessary.

The combination of platinum with silver and, in particular, lead has proved particularly suitable.

The hydroxybenzyl alcohols to be employed as starting compounds preferably correspond to the general formula

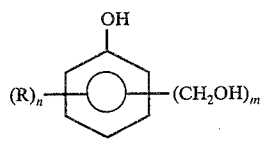

in which
$m$ represents 1, 2 or 3,
$n$ represents the number which results from the difference $(5 - m)$ and the radicals R independently of one another represent hydrogen, alkyl, aryl, alkoxy, hydroxyl, halogen, carboxyl or a fused ring.

Particularly preferred substitutents R are alkyl and alkoxy groups with 1 to 12 carbon atoms, especially the methyl, ethyl, propyl, isopropyl, butyl, pentyl, hexyl and phenyl group, as well as chlorine, bromine and iodine atoms.

The hydroxybenzyl alcohols of the formula I are in themselves known or can be prepared according to known processes, for example by an addition of one, or optionally several, mols of formaldehyde with 1 mol of phenol, cresols, xylenols, ethylphenols, propylphenols, isopropylphenols, butylphenols or the monomethyl ethers, monoethyl ethers, monopropyl ethers and monobutyl ethers of pyrocatechol, of reserocinol and of hydroquinone; monochlorophenols, dichlorophenols, trimethylphenols, trichlorophenols or dimethoxyphenols (see, for example, J. F. Walker, "Formaldehyd" ("Formaldehyde"), Reinhold Publishers, 3rd edition, 1964, pages 304 et seq.; and DT-AS (German Published Specification No.) 1,261,517).

Representatives of these hydroxybenzyl alcohols which may be mentioned by way of example are: 2-hydroxybenzyl alcohol (saligenin), 3-hydroxybenzyl alcohol, 4-hydroxybenzyl alcohol, 2-hydroxy-3-methyl-benzyl alcohol, 2-hydroxy-4-methyl-benzyl alcohol, 2-hydroxy-5-methyl-benzyl alcohol, 4-hydroxy-3-methylbenzyl alcohol, 2-hydroxy-3-ethyl-benzyl alcohol, 2-hydroxy-4-ethyl-benzyl alcohol, 2-hydroxy-5-ethyl-benzyl alcohol, 4-hydroxy-3-ethyl-benzyl alcohol, 4-hydroxy-3,5-dimethyl-benzyl alcohol, 4-hydroxy-2-methyl-5-isopropyl-benzyl alcohol, 4-hydroxy-3,5-di-tert.-butyl-benzyl alcohol, 3,5-dihydroxybenzyl alcohol, 4-hydroxy-3-methoxybenzyl alcohol, 4-hydroxy-3-ethoxybenzyl alcohol, 3-hydroxy-4-methoxy-benzyl alcohol, 2-hydroxy-3-methoxy-benzyl alcohol, 2-hydroxy-4-ethoxybenzyl alcohol, 3-hydroxy-4-isopropoxy-benzyl alcohol, 2-hydroxy-3-chloro-benzyl alcohol, 4-hydroxy-3-chloro-benzyl alcohol, 2-hydroxy-3,5-dichloro-benzyl alcohol, 3,4-dihydroxybenzyl alcohol, 2,4-dihydroxy-benzyl alcohol, 2,5-dihydroxy-benzyl alcohol, 4-hydroxy-3,4-dimethoxy-benzyl alcohol, 2,6-bis(hydroxymethyl)-phenol, 2,4,6-tris-(hydroxymethyl)-phenol, 2,6-bis-(hydroxy-methyl)-4-methyl-phenol, 2,6-bis-(hydroxymethyl)-4-cyclohexyl-phenol, 2,6-bis-(hydroxymethyl)-4-phenyl-phenol, 2,6-bis-(hydroxymethyl)-4-methoxy-phenol, 2,4-bis-(hydroxymethyl)-6-methoxy-phenol, 2,4-bis-(hydroxymethyl)-6-cyclohexylphenol, 2,6-bis-(hydroxymethyl)-4-chloro-phenol, 2,4-bis-(hydroxymethyl)-6-chloro-phenol, 1-hydroxymethyl-2-naphthol, 4-hydroxymethyl-1-naphthol, 2-hydroxymethyl-1-naphthol, 3-hydroxymethyl-1-naphthol and 2-hydroxy-1-hydroxymethylanthracene.

Mixtures of different hydroxybenzyl alcohols can also be employed for the oxidation. If the starting compounds contain several hydroxymethyl groups the oxidation reaction can be so conducted that only one or two of the various hydroxymethyl groups are selectively oxidised to an aldehyde group.

Hydroxybenzaldehydes which contain hydroxymethyl groups are obtained in this way.

The process according to the invention is usually carried out by bringing oxygen or oxygen-containing gases, such as air, into good contact with the alkaline solution, which contains the platinum metal catalyst and the activator according to the invention, of the hydroxybenzyl alcohol. The reaction is usually carried out under atmospheric pressure (1 bar), but the oxidation can also be carried out under elevated or reduced pressures, for example in the range from 0.5 to 10 bars. The course of the reaction can be followed by means of the amount of oxygen taken up and the reaction is discontinued when the amount of oxygen theoretically required for the desired aldehyde has been taken up. Usually, the absorption of oxygen automatically ceases or slows down at this stage. The progress of the reaction can also be followed by other means, for example by determining the hydroxybenzyl alcohol consumed or the hydroxybenzaldehyde formed.

For working up, the platinum metal catalyst, together with undissolved activator, is separated off from the reaction mixture. The aldehydes are liberated from the alkaline reaction solution by acidifying to a pH value below 6 and are separated off by known processes, such as decanting, filtering off, extracting and/or by steam distillation and, if required, are further purified by recrystallisation, distillation, extraction and the like.

The sequence in which the platinum metal catalyst, the activator, the alkali and the hydroxybenzyl alcohol are added together is arbitrary. Thus, the platinum metal catalyst and the activator can be added to the aqueous-alkaline solution of the hydroxybenzyl alcohol; it is also possible initially to introduce the platinum metal catalyst and the activator and to add the aqueous-alkaline solution of the hydroxybenzyl alcohol; finally, it is also possible initially to introduce the platinum metal catalyst, some of the aqueous alkali and the activator and to add the hydroxybenzyl alcohol together with the remaining alkali. Furthermore, it is possible to add the activator to a mixture of the reaction components.

The concentration of the hydroxybenzyl alcohol in the aqueous-alkaline reaction solution is generally so chosen that both the hydroxybenzyl alcohol and the aldehyde formed are in a dissolved form during the reaction. Concentrations of 5 to 30% by weight of hydroxybenzyl alcohol have proved suitable. Mixtures of different hydroxybenzyl alcohols can also be oxidised.

If hydroxybenzyl alcohols which are sparingly soluble or insoluble in the aqueous-alkaline reaction medium are employed as the starting compounds for the process according to the invention and/or if the hydroxybenzaldehydes formed are sparingly soluble or insoluble in the aqueous-alkaline solution, it is possible for the oxidation not to take place, to proceed very slowly or to cease after a short time. It has now been found that the oxidation can be carried out without difficulty even when sparingly soluble or insoluble compounds of this type are employed and/or are formed, if the reaction is carried out in the presence of a solvent for the sparingly soluble or insoluble compound.

The solvent can be completely or partially miscible, or immiscible, with the aqueous-alkaline reaction medium. It is essential that the solvent is inert under the reaction conditions. The particular solvent and amount of solvent to be employed in a particular case can easily be determined by preliminary experiments. Solvents which can be used are both aprotic solvents, such as benzene, hexane, dioxane or acetone, and protic solvents, such as tert.-butanol.

The oxidation is preferably carried out in the presence of alkali, for example sodium hydroxide or potassium hydroxide. The alkali is advantageously used in amounts such that there are 0.3 to 3, preferably 0.75 to 2.5, equivalents of alkali per 1 mol of acid groups in the hydroxybenzyl alcohol. Preferably, about 1 equivalent of alkali is employed per mol of acid groups in the hydroxybenzyl alcohol.

The reaction temperature depends, inter alia, on the stability to heat of the hydroxybenzyl alcohols and/or of the aldehydes to be prepared.

Preferably, the reaction is carried out at temperatures below 100° C. and preferably at about 20° to 60° C.

Foreign substances, for example impurities, in the hydroxybenzyl alcohols, originating from the preparation, such as phenols, boric acid and metal catalysts, in general do not have an adverse effect on the oxidation process according to the invention.

The hydroxybenzaldehydes which can be prepared by the process according to the invention are important organic intermediate products and of great significance for the preparation of aroma substances.

EXAMPLE 1

0.62 g of platinum-containing active charcoal (platinum content: 1% by weight), 20 ml of 1 N sodium hydroxide solution and 0.5 ml of 0.5 molar lead nitrate solution (corresponding to a lead amount of $2.5 \times 10^{-3}$ mols per mol of saligenin) are mixed in a reaction vessel provided with a stirrer, a thermometer and a gas line and a solution of 12.4 g (0.1 mol) of saligenin in 80 ml of 1 N sodium hydroxide solution is added.

After displacement of the air from the reaction vessel by oxygen, pure oxygen is passed under normal pressure into the mixture at 30° C., whilst stirring vigorously and cooling. After 20 minutes, 0.05 mol of oxygen has been taken up and the absorption of oxygen ceases.

After the catalyst has been separated off, the reaction solution is acidified to pH 1 with 50% strength sulphuric acid and the salicylaldehyde liberated is distilled off with steam. The salicylaldehyde is obtained from the distillate by decanting off the organic phase and extracting the aqueous phase with ether. The salicylaldehyde which has been decanted off is combined with the ether extract and the ether solution is dried over sodium sulphate. After evaporating the ether in vacuo, the salicylaldehyde (purity: 99%) is obtained in a yield of 11.1 g (= 90% of theory).

The solution which remains as the distillation residue from the steam distillation is pale yellowish in colour, clear and virtually free from tar deposits.

If the oxidation is carried out without the addition of lead nitrate, virtually no oxygen is taken up in the course of one hour.

The catalyst which has been separated off is washed with water and — in order to enable it to be removed from the filter with lower losses — with a little acetone and is dried briefly. The catalyst recovered in this way is re-employed for the oxidation of saligenin. A further 12.4 g of saligenin, dissolved in 100 ml of 1 N sodium hydroxide solution, was oxidised under the reaction conditions described above. Working up of the reaction mixture is also carried out as described above. The yield of salicylaldehyde is again 90% of theory, relative to saligenin employed. The recovered catalyst is re-employed for the oxidation of saligenin.

The catalyst is re-used a total of 30 times without further platinum metal catlayst or lead nitrate being added to the reaction mixture. The salicylaldehyde yields remain constant at 85–90%. The experiments were then discontinued.

Due to the re-use of the catalyst, the amount of platinum employed per mol of saligenin is reduced to about 2 mg and the amount of lead is reduced to 8.3 − $10^{-5}$ mols.

EXAMPLE 2

The procedure is as described in Example 1 except that 2.5 × $10^{-3}$ mols of lead, in the form of finely powdered (a) metallic lead, (b) lead-II oxide, (c) lead-II sulphate, (d) lead-II acetate, (e) lead-II,IV oxide (mixtures) or (f) lead-IV oxide per mol of saligenin are added, in place of lead-II nitrate solution, to the mixture to be oxidised. In all cases the reaction time is again 20 minutes and the yields are 86 to 90% of theory. If the determination of the yield is carried out not — as in Example 1 — by steam distillation but by titration by the hydroxylamine hydrochloride method, the yields are found to be 93–97% of theory.

EXAMPLE 3

The procedure followed is as described in Example 1 except that an equal volume (100 ml) of 2.5 N sodium hydroxide solution is used in place of 1 N sodium hydroxide solution. The reaction time is 25 minutes and the yield of salicylaldehyde is 88% of theory.

It can be seen from this example that an increase in the amount of alkali to a molar ratio of sodium hydroxide solution/saligenin of 2.5:1 results neither in an improvement of the yields nor in a shortening of the reaction times, but that at least the same yield and the same reaction times are already achieved with less than half the amount of alkali, as is used in Example 1.

If the oxidation of 0.1 mol of saligenin is carried out as described in Example 1 except that the reaction is carried out at a temperature of 60° C., the reaction time is again 20 minutes and the yield of salicylaldehyde is 89% of theory. If the oxidation of 0.1 mol of saligenin is carried out as described in Example 1 except that only 15 mg (= 7.2 × $10^{-5}$ mols) of lead, in the form of a 0.01 N lead-II nitrate solution, are added per mol of saligenin, the reaction time is 22 minutes and the yield of salicylaldehyde is 89% of theory.

EXAMPLE 4

The procedure followed is as described in Example 1 except that the catalyst used is an active charcoal which contains lead and platinum and has been prepared by impregnating 0.62 g of platinum-containing active charcoal (platinum content: 1% by weight) with 5 ml of a solution containing 80 mg of lead-II nitrate and subsequently drying in vacuo at 50° C. The amount of lead employed per mol of saligenin is 2.4 × $10^{-3}$ mols. The oxidation time is 25 minutes and the yield of salicylaldehyde is 88% of theory.

EXAMPLE 5

The procedure followed is as described in Example 1 except that the amount of the platinum-containing active charcoal (platinum content: 1% by weight), and thus the amount of platinum employed per mol of saligenin, is changed for each experiment. The platinum/lead ratio is kept constant.

Table I shows the amounts of platinum and lead employed per mol of saligenin and the yields of salicylaldehyde obtained and the reaction times used to obtain these yields:

Table I

| Amount of platinum [mg] employed per mol of saligenin | Amount of lead [mols] | Reaction time [hours] | Yield of salicylaldehyde [% of theory] |
|---|---|---|---|
| 62 | 2.5 × $10^{-3}$ | 0.33 | 88 |
| 31 | 1.25 × $10^{-3}$ | 1.25 | 85 |
| 16 | 6.5 × $10^{-4}$ | 6 | 84 |
| 8 | 3.2 × $10^{-4}$ | 10 | 84 |

EXAMPLE 6

The procedure followed is as described in Example 1 except that platinum-containing active charcoals with different platinum contents are employed. The amount of lead is 2.5 × $10^{-3}$ mols per mol of saligenin in all experiments.

The results given in Table II are obtained:

Table II

| Contact catalyst | | amount of platinum [mg] employed per mol of saligenin | reaction time [hours] | yield of salicylaldehyde [% of theory] |
|---|---|---|---|---|
| % by weight of contact catalyst, relative to saligenin | platinum content of the contact catalyst [% by weight] | | | |
| 5 | 1 | 62 | 0.33 | 88 |
| 5 | 0.5 | 31 | 1 | 81 |
| 10 | 0.1 | 12 | 8 | 83 |

EXAMPLE 7

6.2 g of platinum-containing active charcoal (platinum content: 1% by weight) and 5 ml of 0.5 molar lead-II nitrate solution are added to a solution of 124 g (1 mol) of saligenin in 400 ml of 2.5 N sodium hydroxide solution (1 mol) (corresponding to 2.5 × $10^{-3}$ mols of lead/mol of saligenin).

After the air in the reaction vessel has been displaced by oxygen, oxygen is passed into the reaction mixture under a pressure of 1 bar, at 40° C. The mixture is stirred so slowly that the absorption of oxygen has ceased only after 5 hours.

Working up of the reaction solution is carried out as described in Example 1. The yield of salicylaldehyde (purity: 99.1%) is 117 g (= 95% of theory). The amount of resin formed during the reaction is less than 1 g even though the reaction was carried out at 40° C. and a long reaction time was chosen.

EXAMPLE 8

0.65 g of platinum-containing active charcoal (platinum content: 1% by weight), 20 ml of 1.75 N sodium hydroxide solution and 5 ml of 1 N silver nitrate solution (corresponding to 5 × $10^{-2}$ mols of silver/mol of saligenin) are stirred in the apparatus described in Example 1. A solution of 12.4 g (0.1 mol) of saligenin in 80 ml. of 1.75 N sodium hydroxide solution is added to the mixture.

After the air in the reaction vessel has been displaced by oxygen, oxygen is passed into the mixture under a pressure of 1 bar, at 30° C., whilst stirring vigorously. After 60 minutes 0.05 mol of oxygen has been taken up and the reaction mixture is worked up as described in Example 1.

The yield of salicylaldehyde (purity: 99%) is 9.1 g (= 73.8% of theory).

EXAMPLE 9

5 ml of 1 N silver nitrate solution (corresponding to 5 × $10^{-2}$ mols of silver per mol of saligenin) and 10 mg of platinum in the form of 1 ml of a dilute $H_2PtCl_6$ solution are added to a solution of 12.4 g (0.1 mol of saligenin in 100 ml of 2 N sodium hydroxide solution, in the apparatus described in Example 1.

After the air has been displaced from the reaction vessel by oxygen, oxygen is passed into the mixture under a pressure of 1 bar in the course of 38 minutes, at 30° C., whilst stirring vigorously. The reaction mixture is then worked up as described in Example 1.

The yield of salicylaldehyde (purity: 99%) is 77% of theory.

If 5 mg of platinum are used in place of 10 mg of platinum, the reaction time is 73 minutes and the yield of salicylaldehyde is 73% of theory.

EXAMPLE 10

5 ml of 1 N silver nitrate solution and 5 mg of palladium in the form of palladium-II nitrate are added to a solution of 12.4 g (0.1 mol) of saligenin in 100 ml of 2 N sodium hydroxide solution, in the apparatus described in Example 1. After the air has been displaced from the reaction vessel by oxygen, oxygen is passed into the mixture under a pressure of 1 bar, at 30° C., whilst stirring vigorously. After 70 minutes 0.05 mol of oxygen has been taken up.

The reaction mixture is worked up as described in Example 1. The yield of salicylaldehyde (purity: 99%) is 60% of theory.

EXAMPLE 11

80 mg of lead-II nitrate (corresponding to 2.4 × $10^{-3}$ mols of lead/mol of hydroxybenzyl alcohol) and 0.62 g of platinum-containing active charcoal (platinum content: 1% by weight) are added to a solution of 12.4 g (0.1 mol) of p-hydroxybenzyl alcohol in 100 ml of 1.5 N sodium hydroxide solution, in the apparatus described in Example 1.

After the air has been displaced from the reaction vessel by oxygen, oxygen is passed into the mixture under a pressure of 1 bar, at 30° C., whilst stirring vigorously. After 20 minutes 0.048 mol of oxygen has been taken up and the absorption of oxygen ceases. After the catalyst has been filtered off, the p-hydroxybenzaldehyde is precipitated by acidifying the filtrate to pH 1 and cooling to about 5° C. After filtering off and drying, the yield of p-hydroxybenzaldehyde is 10.4 g (= 85.4% of theory) (melting point: 115°–116° C.).

EXAMPLE 12

50 mg of tellurium powder (corresponding to 3.9 × $10^{-3}$ mols of tellurium/mol of saligenin) and 1.25 g of platinum-containing active charcoal (platinum content: 1% by weight) are added to a solution of 12.4 g (0.1 mol) of saligenin in 100 ml of 1.5 N sodium hydroxide solution, in the apparatus described in Example 1.

After the air has been displaced from the reaction mixture by oxygen, oxygen is passed into the mixture under a pressure of 1 bar, at 30° C., whilst stirring vigorously. The reaction is discontinued after 100 minutes, when the absorption of oxygen has slowed down to a very great extent. According to the thin layer chromatogram, the solution contains about 2.5 g of unconverted saligenin at this time.

The reaction mixture is worked up as described in Example 1. The yield of salicylaldehyde (purity: 99%) is 8.9 g (= 90%, relative to converted saligenin).

If 50 mg of tellurium-IV oxide (corresponding to 3.1 × $10^{-3}$ mols of tellurium/mol of saligenin) are used in place of the 50 mg of elementary tellurium, the absorption of oxygen again comes almost to a standstill after about 100 minutes. According to the thin layer chromatogram, the reaction solution contains about 3 g of saligenin.

The reaction mixture is worked up as described in Example 1. The yield of salicylaldehyde (purity: 99%) is 8.3 g (= 90% relative to converted saligenin).

EXAMPLE 13

1.25 g of palladium-containing active charcoal (palladium content: 5% by weight and 0.05 g of tellurium powder (corresponding to 3.9 × $10^{-3}$ mols of tellurium/mol of saligenin) are added to a solution of 12.4 g (0.1 mol) of saligenin in 100 ml of 1 N sodium hydroxide solution and the oxidation is carried out under the reaction conditions described in Example 1. After 3.6 hours approximately 0.05 mol of oxygen has been taken up. The reaction mixture is worked up as described in Example 1.

The yield of salicylaldehyde (purity: 99%) is 8.6 g (= 70.5% of theory).

Without the addition of tellurium, 45 hours are required for the absorption of the same amount of oxygen and the yield of salicylaldehyde is only 8 g (= 65% of theory).

EXAMPLE 14

1.25 g of platinum-containing active charcoal (platinum content: 1% by weight) and 0.05 g of tin-IV oxide (corresponding to 3.3 × $10^{-3}$ mols of tin/mol of saligenin) are added to a solution of 12.4 g (0.1 mol) of saligenin in 100 ml of 1 N sodium hydroxide solution. The oxidation is carried out under the reaction conditions described in Example 1. After stirring for 15 hours, approximately 200 ml of oxygen have been taken up and it is possible to detect, in the reaction mixture, 1.8 g of salicylaldehyde by titration and about 10 g of saligenin by thin layer chromatography. The yield of salicylaldehyde is about 75%, relative to converted saligenin.

Without the addition of tin-IV oxide, less than 30 ml of oxygen are taken up in the course of 15 hours.

If 0.63 g of palladium-containing active charcoal (palladium content: 5% by weight) is employed in place of 1.25 g of platinum-containing active charcoal (platinum content: 1% by weight), 0.04 mol of oxygen is taken up in the course of 20 hours. About 2 g of unchanged saligenin can be detected in the reaction mixture by thin layer chromatography.

After the reaction mixture has been worked up as described in Example 1, the yield of salicylaldehyde (purity: 99%) is 6.6 g (= 65% relative to converted saligenin).

EXAMPLE 15

0.65 g of platinum-containing active charcoal (platinum content: 1% by weight) and 0.5 ml of 0.5 molar lead-II nitrate solution (corresponding to 2.5 × $10^{-3}$ mols of lead/mol of hydroxybenzyl alcohol) are added to a solution of 15.2 g (0.1 mol) of 4-hydroxy-3,5-dimethyl-benzyl alcohol in 110 ml of 1.1 N sodium hydroxide solution.

After the air has been displaced from the reaction vessel of oxygen, oxygen is passed into the mixture under a pressure of 1 bar, at 30° C., whilst stirring vigorously. After 25 minutes, the reaction mixture has taken up 0.05 mol of oxygen and the absorption of oxygen ceases.

After filtering off the catalyst, acidifying the filtrate to pH 1 with 50% strength sulphuric acid and cooling, the 4-hydroxy-3,5-dimethyl-benzaldehyde which has precipitated is filtered off. Yield: 14.4 g (96% of theory); melting point: 114° C.

EXAMPLE 16

A solution of 18 g (0.1 mol) of 4-hydroxy-2-methyl-5-isopropyl-benzyl alcohol in 110 ml of 1.1 N sodium hydroxide solution is added to a suspension which has been prepared from 10 ml of 1.1 N sodium hydroxide solution, 0.5 ml of 0.5 molar lead-II nitrate solution and 0.65 g of platinum-containing active charcoal (platinum content: 1% by weight).

After the air has been displaced from the reaction vessel by oxygen, oxygen is passed into the mixture under a pressure of 1 bar, at 30° C., whilst stirring vigorously. After 55 minutes the absorption of oxygen ceases.

After filtering off the catalyst and acidifying the filtrate to pH 1, the 4-hydroxy-2-methyl-5-isopropyl-benzaldehyde which has precipitated is filtered off. Yield: 17.7 g (= 99% of theory) of white crystals with a melting point of 132° C.

EXAMPLE 17

0.5 ml of 0.5 molar lead-II nitrate solution (corresponding to $2.5 \times 10^{-3}$ mols of lead/mol of hydroxybenzyl alcohol) and 0.65 of platinum-containing active charcoal (platinum content: 1% by weight) are added to a solution of 15.4 g (0.1 mol) of 4-hydroxy-3-methoxy-benzyl alcohol in 100 ml of 1 N sodium hydroxide solution.

After the air has been displaced from the reaction vessel by oxygen, oxygen is passed into the mixture under a pressure of 1 bar, at 30° C., whilst stirring vigorously. After 35 minutes the absorption of oxygen ceases.

After filtering off the catalyst and acidifying the filtrate to pH 1 with 50% strength sulphuric acid, the 4-hydroxy-3-methoxy-benzaldehyde which has precipitated is filtered off and dried. Yield: 11.8 g (= 77.6% of theory), melting point: 80°–81° C.

A further 2 g (about 13% of theory) of 4-hydroxy-3-methoxy-benzaldehyde with a melting point of 71°–75° C. are obtained by extracting the filtrate with ether.

EXAMPLE 18

A solution of 8.4 g (0.05 mol) of 2-hydroxy-3-hydroxymethyl-5-methyl-benzyl alcohol in 90 ml of 1 N sodium hydroxide solution is added to a mixture of 10 ml of 1 N sodium hydroxide solution, 0.5 ml of 0.5 molar lead-II nitrate solution (corresponding to $5 \times 10^{-3}$ mols of lead/mol of hydroxybenzyl alcohol) and 0.6 g of platinum-containing active charcoal (platinum content: 1% by weight).

After the air in the reaction vessel has been displaced by oxygen, oxygen is passed into the mixture under a pressure of 1 bar, at 30° C., whilst stirring vigorously. After about 0.035 mol of oxygen has been taken up, a yellow precipitate (sodium salt of the dialdehyde) starts to separate out. This does indeed slow down, but does not prevent, the absorption of oxygen. After 45 minutes the amount of oxygen necessary to form the dialdehyde (that is to say 0.05 mol) has been taken up and the reaction ceases.

The precipitate is dissolved by adding 160 ml of water. After filtering off the catalyst and acidifying the filtrate to pH 1 with 50% strength sulphuric acid, the 2-hydroxy-3-formyl-5-methyl-benzaldehyde which has precipitated is washed with water and dried. Yield: 7.8 g (= 90% of theory), melting point: 122°–124° C.

EXAMPLE 19

0.5 ml of 0.5 molar lead-II nitrate solution (corresponding to $2.6 \times 10^{-3}$ mols of lead-mol of hydroxybenzyl alcohol) and 0.65 g of platinum-containing active charcoal (platinum content: 1% by weight) are added to a solution of 16 g (0.095 mol) of 2-hydroxy-3-hydroxymethyl-5-methyl-benzyl alcohol in 120 ml of 1.1 N sodium hydroxide solution.

After the air has been displaced from the reaction vessel by oxygen, 0.048 mol (1,200 ml) of oxygen is passed into the mixture under a pressure of 1 bar, at 30° C., whilst stirring well (time required: 45 minutes).

After filtering off the catalyst and acidifying the filtrate to pH 1 with 50% strength sulphuric acid, the product which has precipitated is filtered off and dried. Yield: 13.3 g of a product which, according to analysis by NMR (the area ratio of the aromatic protons was evaluated), has the following composition: 69% of 2-hydroxy-3-hydroxymethyl-5-methyl-benzaldehyde (doublet at 7.2–7.4 ppm), 18% of 2-hydroxy-3-formyl-5-methyl-benzaldehyde (singlet at 7.8 ppm) and 13% of 2-hydroxy-3-hydroxymethyl-5-methyl-benzyl alcohol (singlet at 6.9 ppm).

The analytical data show that essentially only one of the two methylol groups has been oxidised; that is to say the selective oxidation of one methylol group can be carried out with the aid of the process according to the invention. Phenols which also contain a hydroxymethyl group in addition to an aldehyde group can be prepared in this way.

The yield of the oxidation product can be further increased, for example, by extraction of the filtrate.

EXAMPLE 20

0.5 ml of 0.5 molar lead-II nitrate solution (corresponding to $2.5 \times 10^{-3}$ mols of lead/mol of hydroxybenzyl alcohol) and 0.65 g of platinum-containing active charcoal (platinum content: 1% by weight) are added to a solution of 19.3 g (0.1 mol) of 2-hydroxy-3,5-dichlorobenzyl alcohol in 125 ml of 7.5% strength sodium hydroxide solution.

After the air has been displaced by oxygen, oxygen is passed into the mixture under a pressure of 1 bar, at 30° C., whilst stirring vigorously. The oxidation product already precipitates shortly after the start of the oxidation but, when the suspension is mixed thoroughly, the absorption of oxygen continues and has ended after 150 minutes, after the theoretically required amount of oxygen (0.05 mol) has been taken up.

The suspension is acidified to pH 1 with 50% strength sulphuric acid, whilst stirring vigorously, and 100 ml of benzene are added in order to dissolve the organic precipitate. The catalyst is then filtered off, the benzene phase of the filtrate is separated off and the aqueous phase of the filtrate is extracted with benzene. The benzene is distilled off from the combined benzene phases in vacuo. 18.1 g (= 94% of theory) of 2-hydroxy-3,5-dichloro-benzaldehyde (melting point: 92°-94° C.) remain.

EXAMPLE 21

0.25 ml of 0.5 molar lead-II nitrate solution (corresponding to 2.5 × $10^{-3}$ mols of lead/mol of hydroxybenzyl alcohol), 0.32 g of platinum-containing active charcoal (platinum content: 1% by weight and 50 ml of benzene are added to a solution of 9.65 g (0.05 mol) of 2-hydroxy-3,5-dichlorobenzyl alcohol in 60 ml of 7.5% strength sodium hydroxide solution.

After the air has been displaced from the reaction vessel by oxygen, oxygen is passed into the mixture under a pressure of 1 bar, at 30° to 35° C., whilst stirring vigorously. After 75 minutes 0.025 mol of oxygen has been taken up and the absorption of oxygen ceases. The reaction mixture is acidified to pH 1 with 50% strength sulphuric acid and the catalyst is filtered off. The benzene phase of the filtrate is separated off and the aqueous phase of the filtrate is extracted with benzene.

The benzene is distilled off from the combined benzene phases in vacuo. 9.5 g (99% of theory) of 2-hydroxy-3,5-dichloro-benzaldehyde (melting point: 90°-94° C.) remain. If the oxidation is carried out in the absence of the organic solvent, the oxidation time increases to 150 minutes.

EXAMPLE 22

0.25 ml of 0.5 molar lead-II nitrate solution, 0.32 g of platinum-containing active charcoal (platinum content: 1% by weight) and 50 ml of n-hexane are added to a solution of 9.65 g (0.05 mol) of 2-hydroxy-3,5-dichlorobenzyl alcohol in 60 ml of 7.5% strength sodium hydroxide solution.

After the air has been displaced from the reaction vessel by oxygen, oxygen is passed into the mixture under a pressure of 1 bar, at 30° to 35° C., whilst stirring vigorously. After 75 minutes 0.025 mol of oxygen has been taken up and the reaction ceases. The pH of the reaction mixture is adjusted to 1 with 50% strength sulphuric acid, the reaction product which has precipitated is brought into solution by adding 50 ml of benzene and the catalyst is filtered off. The organic layer of the filtrate is separated off and the aqueous layer is extracted with benzene. Benzene and n-hexane are distilled off from the combined organic phases in vacuo. 9.5 g (= 99% of theory) of 2-hydroxy-3,5-dichloro-benzaldehyde (melting point: 92°-94° C.) remain.

If the oxidation is carried out in the absence of the organic solvent, the oxidation time increases to 150 minutes.

EXAMPLE 23

0.25 ml of 0.5 molar lead-II nitrate solution (corresponding to 2.5 × $10^{-3}$ mols of lead/mol of hydroxybenzyl alcohol), to 2.5 × $10^{-3}$ muls of lead/mol of hydroxybenzyl alcohol), 0.32 g of platinum-containing active charcoal (platinum content: 1% by weight) and 50 ml. of tert.-butanol are added to a solution of 9.65 g (0.05 mol) of 2-hydroxy-3,5-dichlorobenzyl alcohol in 60 ml of 7.5% strength sodium hydroxide solution.

After the air has been displaced from the reaction vessel by oxygen, oxygen is passed into the mixture under a pressure of 1 bar, at 30° to 35° C., whilst stirring vigorously. After 45 minutes 0.025 mol of oxygen has been taken up and the absorption of oxygen ceases. The reaction mixture is acidified to pH 1, the reaction product which has precipitated is brought completely into solution by adding 50 ml of benzene and the catalyst is filtered off. The organic layer of the filtrate is separated off and the aqueous layer of the filtrate is extracted with benzene. Tert.-butanol and benzene are distilled off from the combined organic phases in vacuo. 9.3 g (= 97% of theory) of 2-hydroxy-3,5-dichloro-benzaldehyde (melting point: 90°-94° C.) remain as the residue.

If the oxidation is carried out in the absence of the organic solvent, the oxidation time increases to 150 minutes.

EXAMPLE 24

A solution of 11.8 g (0.05 mol) of 4-hydroxy-3,5-di-tert.-butyl-benzyl alcohol in 50 ml of tert.-butanol is added to a suspension of 0.6 g of platinum-containing active charcoal (platinum content: 1% by weight), 0.5 ml of 0.5 molar lead-II nitrate solution (corresponding to 5 × $10^{-3}$ mols of lead/mol of hydroxybenzyl alcohol) and 50 ml of 1 N sodium hydroxide solution.

After the air has been displaced from the reaction vessel by oxygen, oxygen is passed into the mixture under a pressure of 1 bar, at 30° to 35° C., whilst stirring vigorously. After 12 minutes 0.025 mol of oxygen (625 ml) has been taken up and the absorption of oxygen ceases. After filtering off the catalyst and acidifying the filtrate to pH 1, the 4-hydroxy-3,5-di-tert.-butyl-benzaldehyde which has precipitated is filtered off, washed with water and dried. Yield: 9.6 g (= 82% of theory), melting point: 182°-186° C. If the oxidation is carried out in the absence of the organic solvent, virtually no oxidation takes place.

EXAMPLE 25

A solution of 11.8 g (0.05 mol) of 4-hydroxy-3,5-di-tert.-butyl-benzyl alcohol in 50 ml of acetone is added to a mixture of 50 ml of 1 N sodium hydroxide solution, 0.6 g of platinum-containing active charcoal (platinum content: 1% by weight) and 5 ml of 0.5 molar lead-II nitrate solution (corresponding to 5 × $10^{-3}$ mols of lead/mol of hydroxybenzyl alcohol).

After the air has been displaced from the reaction vessel by oxygen, oxygen is passed into the mixture for 10 minutes under a pressure of 1 bar, at 30° C., whilst stirring vigorously. The catalyst is then filtered off and the filtrate is acidified to pH 1 with 50% strength sulphuric acid. The precipitate which has separated out is filtered off and dried. 9.6 g of a product which contains 51% by weight of 4-hydroxy-3,5-di-tert.-butyl-benzaldehyde in addition to unconverted starting material are obtained.

The aldehyde content was determined titrimetrically by the hydroxylamine hydrochloride method and the starting material was detected by thin layer chromatography. The IR spectrum of the product agrees with the IR spectrum of the 4-hydroxy-3,5-di-tert.-butyl-benzaldehyde prepared by another route. If the oxidation is carried out in the absence of the organic solvent, virtually no oxidation takes place.

EXAMPLE 26

A solution of 11.8 g (0.05 mol) of 4-hydroxy-3,5-di-tert.-butyl-benzyl alcohol in 50 ml of dioxane is added to a mixture of 50 ml of 1 N sodium hydroxide solution, 0.6 g of platinum-containing active charcoal (platinum content: 1% by weight) and 0.5 ml of 0.5 molar lead-II nitrate solution (corresponding to 2.5 × 10⁻³ mols of lead/mol of hydroxybenzyl alcohol).

After the air has been displaced from the reaction vessel by oxygen, oxygen is passed into the mixture for 25 minutes under a pressure of 1 bar, at 30° C., whilst stirring vigorously. The catalyst is then filtered off and the filtrate is acidified to pH 1 with dilute sulphuric acid. The product which has precipitated is filtered off and dried. 8.6 g of a product which has a IR spectrum identical to the IR spectrum of 4-hydroxy-3,5-di-tert.-butyl-benzaldehyde were obtained. The aldehyde content, determined titrimetrically, is 60%. According to the thin layer chromatogram, the product contained 40% of starting material. If the oxidation is carried out in the absence of the organic solvent, virtually no oxidation takes place.

EXAMPLE 27

0.6 g of platinum-containing active charcoal (platinum content: 1% by weight) (corresponding to 60 mg of platinum per mol of hydroxymethyl group) and 0.5 ml of 0.5 molar lead-II nitrate solution (corresponding to 5 × 10⁻³ mols of lead/mol of phenol) are added to a solution of 11.5 g (0.05 mol) of 2,6-(bis-(hydroxymethyl)-4-phenyl-phenol (melting point: 108°–110° C.) in 90 ml of 1 N sodium hydroxide solution.

After the air has been displaced from the reaction vessel by oxygen, oxygen is passed into the mixture under a pressure of 1 bar, at 30° C., whilst stirring vigorously. The reaction product already starts to precipitate shortly after the reaction has started. After 4 hours the 0.025 mol of oxygen required for the oxidation of one methylol group has been taken up and the reaction is discontinued.

250 ml of ethyl acetate are added to the reaction mixture and the mixture is rendered slightly acid, whilst stirring. The oxidation product then goes into solution in the ethyl acetate. The catalyst is then filtered off and the ethyl acetate phase of the filtrate is separated off and concentrated to dryness in a rotary evaporator. 10.1 g of residue are obtained and the aldehyde group content indicates that this consists to the extent of 98% of the monoaldehyde.

After recrystallisation of the product from benzene, 6.4 g (=56% of theory) of 2-hydroxymethyl-6-formyl-4-phenylphenol are obtained in the form of pale yellow crystals (melting point: 122° C.). The NMR spectrum of the product confirms the structure: singlets (intensity) at 2.5 (1), 4.8 (2), 10.2 (1) and 11.5 (1) ppm; multiplet (intensity) 7.2–7.8 (7) ppm.

What is claimed is:

1. In the process for the production of hydroxybenzaldehydes by oxidation of hydroxybenzyl alcohols of the formula

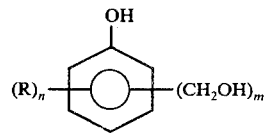

in which
m represents 1, 2 or 3 and
n represents the number which results from the difference (5 − m) and the radicals R independently of one another represent hydrogen, alkyl, aryl, alkoxy, hydroxyl, halogen, carboxyl or a fused ring, with oxygen or oxygen-containing gases in an aqueous alkaline medium at a temperature in the range of 0 to 100° C. in the presence of a platinum metal catalyst, the improvement comprising carrying out the oxidation in the presence of lead and/or compounds thereof.

2. The process according to claim 1, wherein lead is employed in amounts of $5 \times 10^{-6}$ to $1 \times 10^{-1}$ mols per mol of hydroxymethyl group to be oxidised.

3. The process according to claim 1, wherein lead is employed in amounts of $1 \times 10^{-5}$ to $1 \times 10^{-2}$ mols per mol of hydroxymethyl group to be oxidised.

4. The process according to claim 1, wherein platinum and/or palladium are used as platinum metal catalyst.

5. The process according to claim 1, wherein lead is used together with a platinum catalyst.

6. The process according to claim 1, wherein active charcoal is used as support for the platinum metal.

7. The process according to claim 1, wherein the platinum metal content of the supported catalyst is less than 6% by weight.

8. The process according to claim 1, wherein the reaction is carried out in the presence of an organic solvent.

* * * * *